US009717413B2

(12) United States Patent
Colvin et al.

(10) Patent No.: US 9,717,413 B2
(45) Date of Patent: Aug. 1, 2017

(54) BIOCOMPATIBLE, HUMAN IMPLANTABLE APPARATUS AND METHOD FOR FULLY ENCASING A CIRCUIT WITHIN A POLYMER HOUSING (75) Inventors: Arthur Earl Colvin, Mt. Airy, MD (US); Carrie R. Lorenz, Woodbine, MD (US); Casey J. O'Connor, Gaithersburg, MD (US); Steven J. Walters, Ellicott City, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

(21) Appl. No.: 13/171,711

(22) Filed: Jun. 29, 2011

(65) Prior Publication Data
US 2011/0255255 A1    Oct. 20, 2011

Related U.S. Application Data (63) Continuation of application No. 10/825,648, filed on Apr. 16, 2004, now abandoned.

(51) Int. Cl.
*H05K 5/00* (2006.01)
*A61B 5/00* (2006.01)
*H05K 5/06* (2006.01)

(52) U.S. Cl.
CPC ........... *A61B 5/0031* (2013.01); *H05K 5/065* (2013.01)

(58) Field of Classification Search
CPC ................... H05K 7/142; H05K 3/284; H01L 2924/01079; H01L 23/10
USPC ........ 361/782–784, 752–753; 174/50.5, 501, 174/504, 521
See application file for complete search history.

(56) References Cited

U.S. PATENT DOCUMENTS

| 4,362,850 | A | * | 12/1982 | Burk ..................... C08F 279/02 525/316 |
| 5,047,627 | A | | 9/1991 | Yim et al. |
| 5,223,851 | A | * | 6/1993 | Hadden et al. ............... 343/873 |
| 5,482,008 | A | | 1/1996 | Stafford et al. |
| 5,827,201 | A | | 10/1998 | Samson et al. |
| 5,833,603 | A | | 11/1998 | Kovacs et al. |
| 5,840,148 | A | | 11/1998 | Campbell et al. |
| 5,894,351 | A | | 4/1999 | Colvin, Jr. |
| 5,910,661 | A | | 6/1999 | Colvin, Jr. |

(Continued)

FOREIGN PATENT DOCUMENTS

| CN | 1303397 A | 7/2001 |
| EP | 0940076 A | 9/1999 |

(Continued)

OTHER PUBLICATIONS

Lovely, D.F., et al., "Epoxy moulding system for the encapsulation of microelectronic devices suitable for implantation," *Medical & Biological Engineering & Computing UK*, vol. 24, No. 2, Mar. 1986, pp. 206-208.

*Primary Examiner* — Tuan T Dinh
(74) *Attorney, Agent, or Firm* — Rothwell, Figg, Ernst & Manbeck, P.C.

(57) ABSTRACT

A biocompatible, human implantable apparatus and a method for fully encasing a circuit within a polymer housing. The method may include placing the circuit in a mold, injecting a formulation into the mold, and polymerizing the formulation. The formulation may include monomers and polymers. The apparatus may include a circuit in a polymerized formulation of monomers and polymers.

18 Claims, 10 Drawing Sheets (56) References Cited

U.S. PATENT DOCUMENTS

| | | |
|---|---|---|
| 5,917,605 A | 6/1999 | Colvin, Jr. |
| 5,963,132 A | 10/1999 | Yoakum |
| 6,304,766 B1 | 10/2001 | Colvin, Jr. |
| 6,330,464 B1 | 12/2001 | Colvin, Jr. et al. |
| 6,371,927 B1 | 4/2002 | Brune et al. |
| 6,420,622 B1 | 7/2002 | Johnston et al. |
| 6,632,907 B1 | 10/2003 | Mizota et al. |
| 6,711,423 B2 | 3/2004 | Colvin, Jr. |
| 7,800,078 B2 | 9/2010 | Colvin et al. |
| 2002/0026108 A1 | 2/2002 | Colvin, Jr. |
| 2002/0167735 A1* | 11/2002 | Jethmalani et al. .......... 359/642 |
| 2003/0048411 A1* | 3/2003 | Jethmalani et al. .......... 351/205 |
| 2003/0181794 A1 | 9/2003 | Rini et al. |
| 2004/0012979 A1 | 1/2004 | Squicciarini |

FOREIGN PATENT DOCUMENTS

| | | |
|---|---|---|
| JP | 4-231850 A | 8/1992 |
| TW | 299225 | 3/1997 |
| WO | WO 93/15651 A1 | 8/1993 |

\* cited by examiner

BIOCOMPATIBLE, HUMAN IMPLANTABLE APPARATUS AND METHOD FOR FULLY ENCASING A CIRCUIT WITHIN A POLYMER HOUSING

This application is a continuation of U.S. patent application Ser. No. 10/825,648, filed Apr. 16, 2004, incorporated herein by reference in its entirety.

BACKGROUND OF THE INVENTION

1. Field of the invention

The present invention relates to a circuit housing, and, more specifically, to a housing for a circuit designed to be implanted in-vivo (i.e., an implantable circuit).

2. Discussion of the Background

There are several applications that require a circuit to be protected from the environment in which the circuit is intended to operate. For example, a human implantable glucose sensor circuit must be housed within a suitable housing to both protect the sensor from the human body and to protect the human body from the sensor. U.S. Pat. No. 6,330,464, the disclosure of which is incorporated herein by this reference, discloses such a sensor.

A housing encasing an implantable circuit should have at least some of the following characteristics: (1) the ability to protect the electronic circuitry of the sensor from the ambient in-vivo chemical and physical environment, (2) the ability to protect tissue adjacent to the sensor from any adverse reaction which could result as a consequence of contact (or leachables) from within the circuitry—in addition, beyond the adjacent tissue, the encasement must not permit leachables of any detectable significance into the general body environment; (3) the ability to permit wireless electronic communication between the circuitry and an external reader for power and signal; (4) the ability to permit free passage of wavelengths of light necessary for optical functioning of the sensor; (5) the ability to support the surface chemistry required to form a chemical recognition "front-end"; (6) the housing should be high volume manufacture-able; (7) the housing must be non-toxic and "biocompatible"; and (8) provide a sufficiently high reliability to meet the specifications of a medical product.

SUMMARY OF THE INVENTION

The present invention provides a housing that meets many of the criteria outlined above. In one aspect, the present invention provides a circuit encased within a completely enclosed polymer housing. Preferably, the housing is made of an organic polymer, such as PMMA. In some embodiments, the circuit is first enclosed within a glass housing which itself is then enclosed within a second housing, such as a housing made from an organic polymer. In other embodiments, the circuit is first encased within a brick of epoxy and then the epoxy brick containing the circuit is enclosed within a housing.

In another aspect, the present invention provides a method for enclosing a circuit in a polymer housing. In one embodiment, the method may include the following steps: (a) placing the circuit in a mold; (b) pouring a formulation into the mold so that the formulation completely surrounds the circuit, wherein the formulation comprises monomers; and (c) polymerizing the monomers. In step (b), all of the formulation need not be poured at once. For example, in some embodiments, the formulation is poured into the mold until the mold is half full and then after a delay additional formulation is poured into the mold. In some embodiments, the monomers may be MMA monomers. The formulation may further comprise pre-polymerized PMMA.

In another embodiment, the method may include the following steps: inserting the circuit into a polymer housing; injecting an optical epoxy into the polymer housing to fill the spaces between the circuit and the inside walls of the housing (in some embodiments the injection is from the bottom up to force out trapped air); capping an open end of the housing; placing the housing containing the optical epoxy and the circuit into a pressure vessel and increasing the pressure and temperature within the vessel; allowing the optical epoxy to cure; and removing the housing from the pressure vessel.

In another embodiment, the method may include the following steps: inserting the circuit into a glass housing; injecting an optical epoxy into the glass housing to fill the spaces between the circuit and the inside walls of the housing; injecting an optical epoxy into a polymer housing; inserting into the polymer housing the glass housing containing the circuit; capping an open end of the glass housing; and capping an open end of the polymer housing.

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

DETAILED DESCRIPTION OF THE PREFERRED EMBODIMENT

Figure 1:
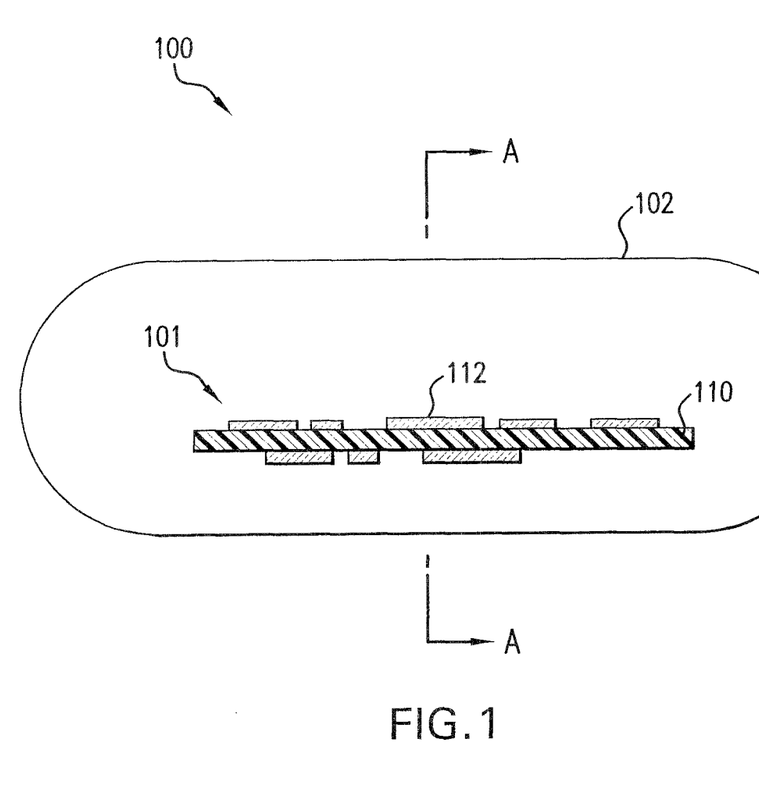
FIG. 1 illustrates one embodiment of a circuit assembly according to the present invention.

FIG. 1 illustrates one embodiment of a circuit assembly 100 according to the present invention. As shown in FIG. 1, the present invention provides an assemblage including a circuit 101 housed within a fully enclosed housing 102. Preferably, as shown in FIG. 1, housing 102 is capsule shaped, but other shapes may be used. Circuit 101 may be an electronic circuit having a printed circuit board 110 and one or more electrical and optical components 112 attached to the circuit board 110. Circuit 101 may include a conventional sensor, such as the sensor described in U.S. Pat. No. 6,304,766. The housing 102 may be a housing made from PMMA, which is a polymer of methyl methacrylate (MMA) monomers, or from other organic polymers.

Figure 2:
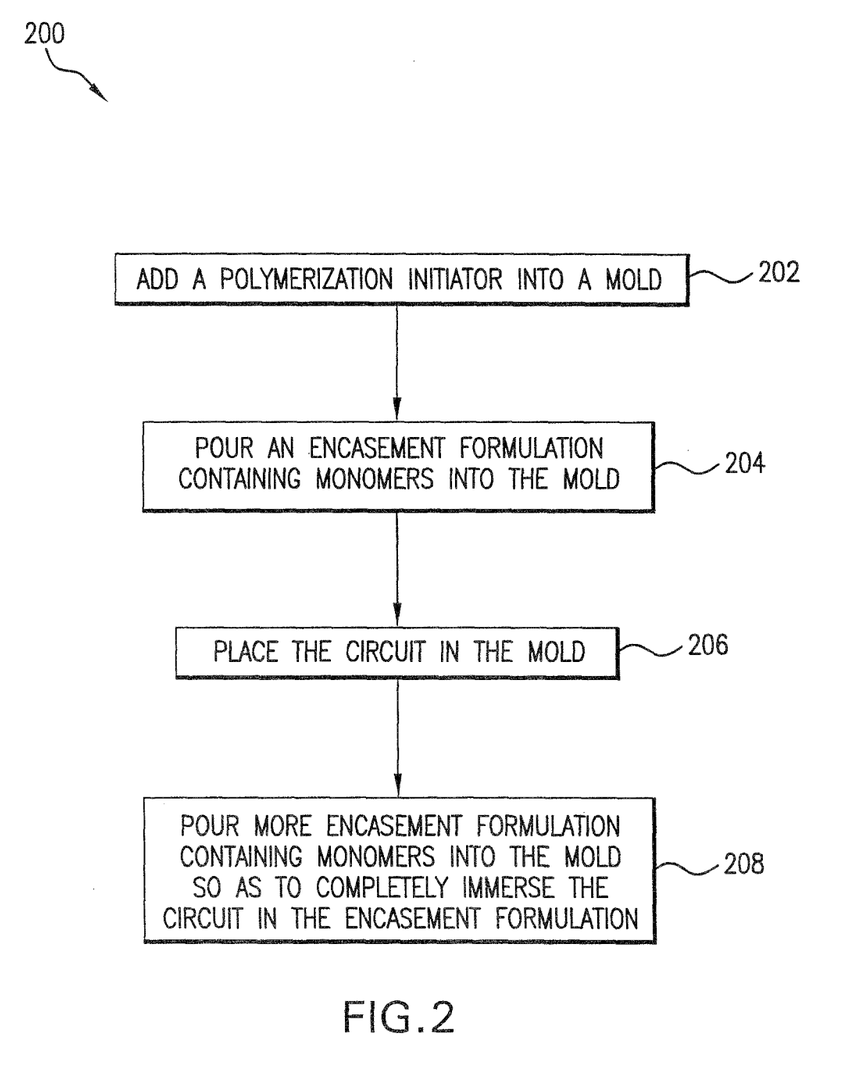
FIG. 2 is a flow chart illustrating a process, according to one embodiment, for encasing a circuit within a polymer housing.

FIG. 2 is a flow chart illustrating a process 200, according to one embodiment, for creating circuit assembly 100. Process 200 may begin in step 202, where a polymerization initiator is added to a mold. In step 204, an encasement formulation containing monomers is poured into the mold (e.g., filling the mold halfway). In step 206, circuit 101 is placed in the mold. In step 208, more of the encasement formulation is poured into the mold so that the circuit is completely immersed in the encasement formulation. In one embodiment, the encasement formulation includes monomers. In one embodiment, the encasement formulation consists of or essentially consists of MMA monomers. In this manner, one can encase circuit 101 in a polymer housing.

In some situations, for example, situations where the formulation includes MMA monomers and circuit 101 is relatively large, circuit 101 can become severely damaged during the polymerization process (i.e., during step 206). The cause of this damage is usually attributed to the shrinkage that occurs naturally during polymerization of MMA. In the joining of bonds between monomers contained within a neat solution of MMA, the intermolecular spacing is reduced within a polymer as the reaction progresses. This is a well-known phenomena and typical of most, if not all, polymer reactions. The net volumetric shrinkage that occurs during the polymerization of PMMA from neat monomer solution is approximately 14%.

This shrinkage can, in some circumstances, create a particular problem when using PMMA as a circuit housing because, as the encasement reaction progresses, and the viscosity increases as the shrinkage occurs simultaneously, the electrical components 112, which are mounted on the circuit board 110 typically with conductive epoxy, are pulled from the circuit board 110 during the polymerization process.

The relative strength of the conductive epoxy used to hold the components 112 in place, which conductive epoxy is formulated primarily and maximally for its electrical conductance and cure properties, does not have sufficient mechanical strength to withstand the pull and stress from PMMA shrinkage as the encasement reaction progresses. Consequently, some attempts to encase a circuit from an MMA monomer encasement formulation result in a non-functional circuit because of un-repairable mechanical damage.

To solve this problem, one aspect of the present invention is a method by which the polymerization reaction can be conducted without damage to the encased circuit 101. Because pre-polymerized PMMA of large molecular weights (approximately up through 1 million+mw) can be dissolved in MMA monomer, and because the shrinkage is a direct result of bonds forming from discrete monomers, one possible solution is to formulate the encasement formulation to include a portion of MMA monomer and a portion of pre-polymerized PMMA dissolved within the MMA monomer.

The net shrinkage is proportional to the amount of monomer which is reacted to become polymer within the overall volume. If the overall encasement formulation volume, is portioned to include, for example, about 70% pre-polymerized PMMA, and about 30% un-reacted MMA monomer (into which the 70% PMMA has been dissolved), then the degree of shrinkage which occurs drops in direct proportion to the monomer component within the overall volume. In practice, an encasement formulation of 100% MMA monomer shrinks volumetrically about 14% overall. By dropping the formulation to only 30% MMA, shrinkage in the amount of approximately 0.3×14=4.3% would be expected. In practice, approximately 4% shrinkage is measured from making this improvement.

Accordingly, the result of altering percent solids provides an improvement in system stress during encasement by reducing shrinkage from, for example, 14% to 4% by reformulating MMA/PMMA specifically for the encasement process. Formulation ratios of 60-80% PMMA in MMA are preferred, although not required, because of a present practical limitation. Although to a point, higher ratio values would be expected to reduce shrinkage proportionately, and further reduction in shrinkage may be possible. As a practical matter, the solution viscosity becomes extremely high at these higher ratio levels making the high solids solution extremely difficult to handle, transfer, etc.

In some situations, however, even with 4% shrinkage, which is a great improvement over 14%, some percentage (about 40-50%) of circuits 101 can not withstand the 4% shrinkage of the encasement. The surviving circuits tend to have greater amounts of conductive epoxy to increase mechanical strength slightly of the surface mounted parts. However, conductive epoxy is not sufficiently strong, and to increase the amount used per connection beyond good manufacturing standards would then create other problems. Another important consideration is for wire-bonded circuits. These "frog hair" gold wires are typically 25 microns in diameter which is about ⅓ to ¼ the diameter of a typical human hair. Small amounts of movement relative to the fixed board components can rip these wires from the attachments.

Accordingly, in some applications, it is desirable to mechanically strengthen the circuit 110 to allow it to withstand the remaining shrinkage from the PMMA encasement cure reaction.

Figure 10A:
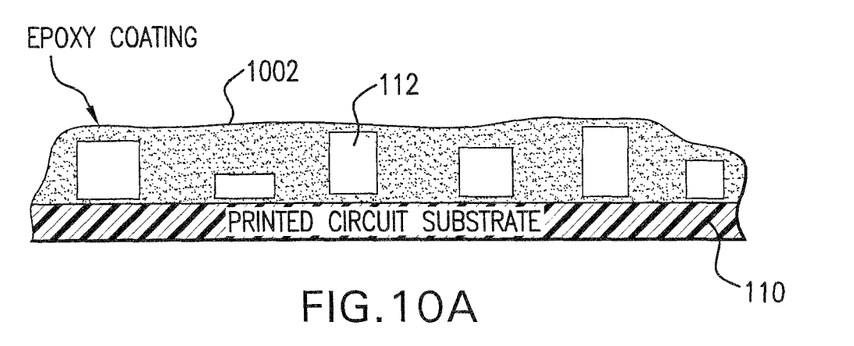
FIGS. 10A and 10B illustrate a circuit covered with different amount of epoxy.
Figure 10B:
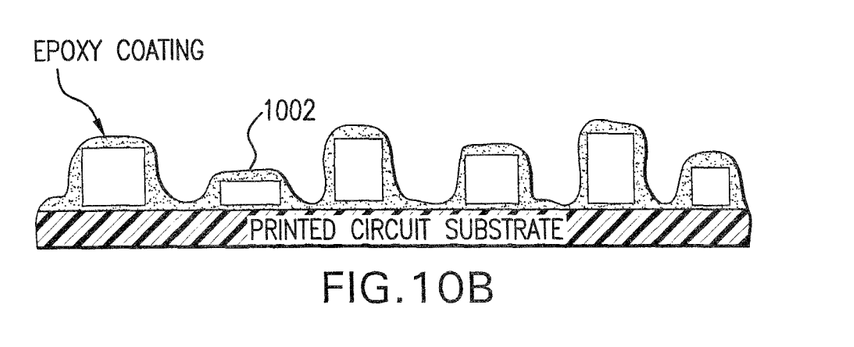

One way to mechanically strengthen circuit 101 to allow it to withstand the remaining 4% shrinkage from the PMMA (70/30) encasement cure reaction, is to reinforce the circuit with a pre-applied epoxy layer. For example, following assembly of the electrical components to the circuit board and cleaning of the assembly, an epoxy is applied over the circuit, which epoxy both under-fills and overfills the components attached to the circuit board. Surprisingly, it was discovered that this solution works best when the applied epoxy covers the components in such a way as to result in a relatively "smooth" surface topology, but this is not a requirement. This "smooth" surface topology is illustrated in FIG. 10A. For comparison, FIG. 10B shows a "non-smooth" epoxy coating. As shown in FIG. 10A, the surface 1002 of the epoxy coating is smooth or substantially smooth.

Although the epoxy adequately strengthens circuit 101 against damage from the shrinking polymer, the resultant stress caused by the remaining 4% shrinkage then becomes manifest as de-lamination between the adjoining surfaces of epoxy and PMMA within the final encasement. As mentioned above, it was discovered that if the surface was smoothed by the volume and application of the epoxy pre-coat, not allowing the PMMA to get a "grip" within the surface topology, then de-lamination was less likely to occur. The stress from the 4% remaining shrinkage is then absorbed as internal stress within the PMMA encasement body itself. This stress may be removed in a conventional way by annealing in a final operation.

Some or all of the epoxy used to reinforce the circuit 110 may, in some embodiments, include a light blocking pigment (such as black or wavelength specific) which prevents unwanted light propagation and scatter about the circuit, thereby increasing the optical signal to noise ratio of the system.

In some embodiments, to prolong the life of the circuitry 101, it may be desirable to prevent molecular water vapor that has seeped through the housing 102 from condensing to become liquid water. If liquid water cannot form from the water vapor, then potential ion contaminants present cannot become solvated, which can lead to circuit failure.

One way to prevent the water vapor from condensing is to prevent the formation of heat induced bubbles in the encasement polymer. MMA monomer is extremely volatile. The polymerization reaction of MMA to PMMA is also exothermic. The exothermic heat yield from a typical reaction begun at room temperature will commonly increase the temperature as the reaction progresses to a point where the remaining un-reacted monomer will boil and create bubbles of all sizes trapped within the cured polymer. To prevent any possibility of heat induced micro-bubbles and voids within the housing where water vapor could condense, substantial overpressure may be used during the polymerization reaction. More specifically, in a preferred embodiment, a mold containing PMMA/MMA is placed within a pressure reactor that is then pressurized to a pressure that exceeds the vapor pressure of MMA monomer at the polymerization temperature. This pressurization process both prevents bubbles and provides a very close mechanical surface bond with the underlying epoxy coat which does not delaminate once formed. The housing is clear and without bubble or void defects to prevent water from condensing, and as an important byproduct, provides excellent optical clarity without bubble defect.

Figure 3:
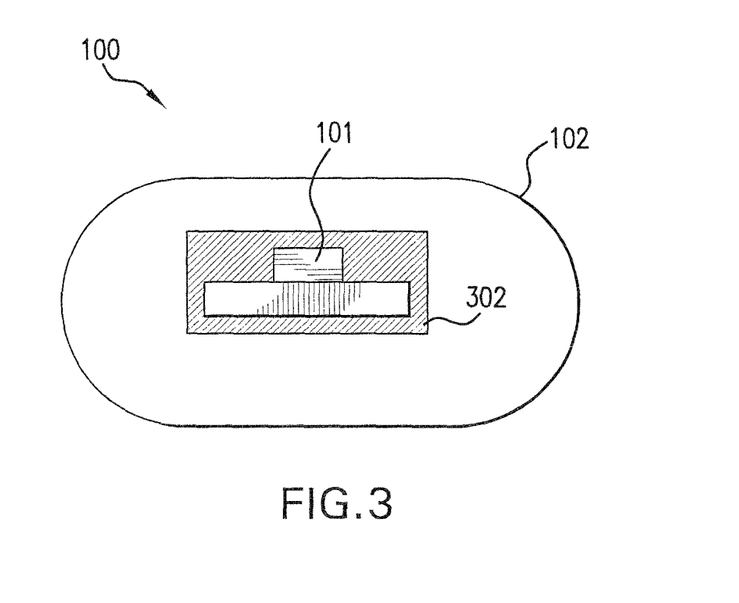
FIG. 3 is a cross sectional view of a circuit assembly according to an embodiment of the invention.

Referring now to FIG. 3, FIG. 3 is a cross sectional view of circuit assembly 100, according to one embodiment, along line A. As shown in FIG. 3, the circuit 101 may be fully encased within a brick of epoxy 302 (or "epoxy brick 302"), which is encased within housing 102.

Figure 4:
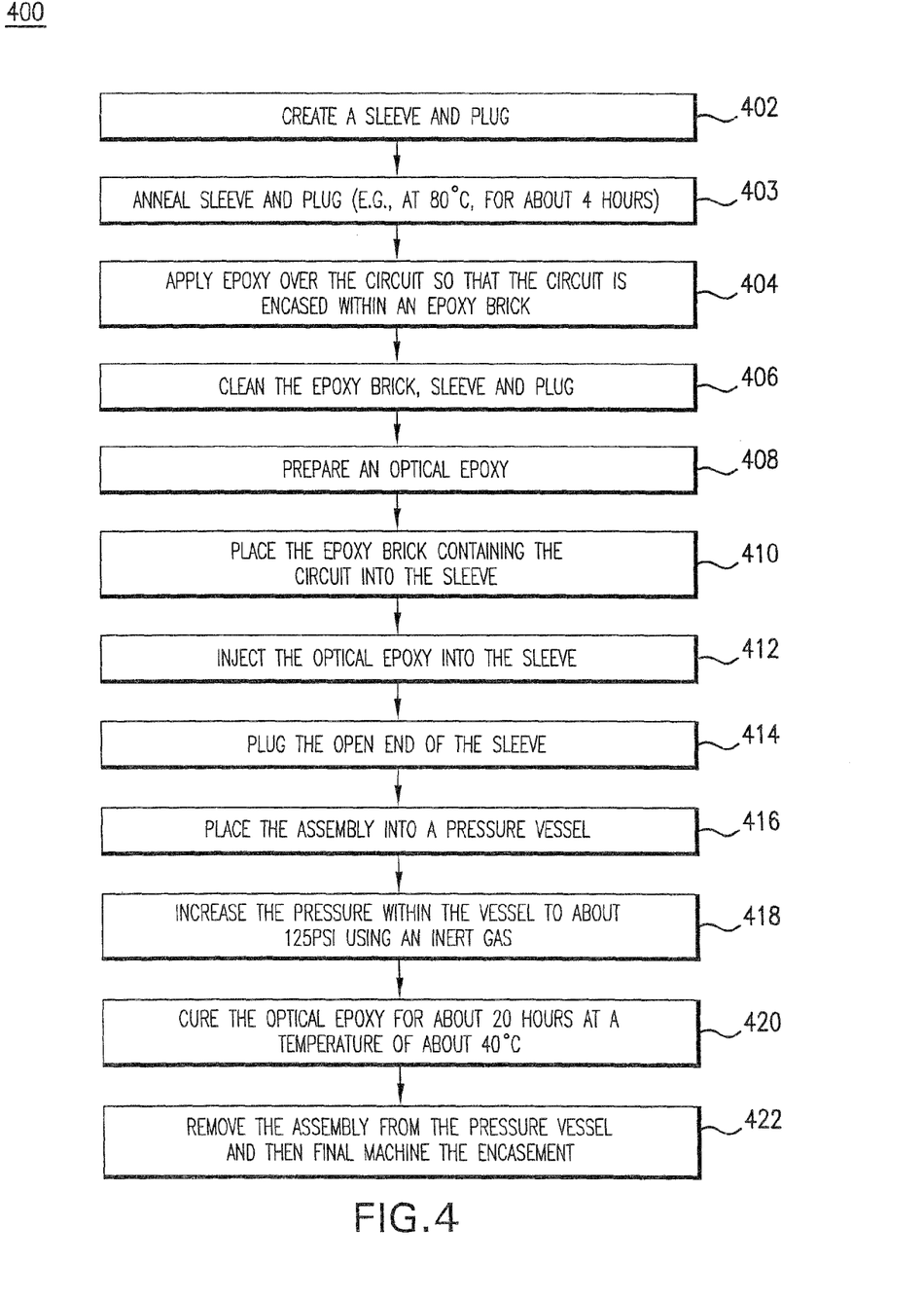
FIG. 4 is a flow chart illustrating a process, according to another embodiment, for encasing a circuit within a polymer housing.
Figure 5:
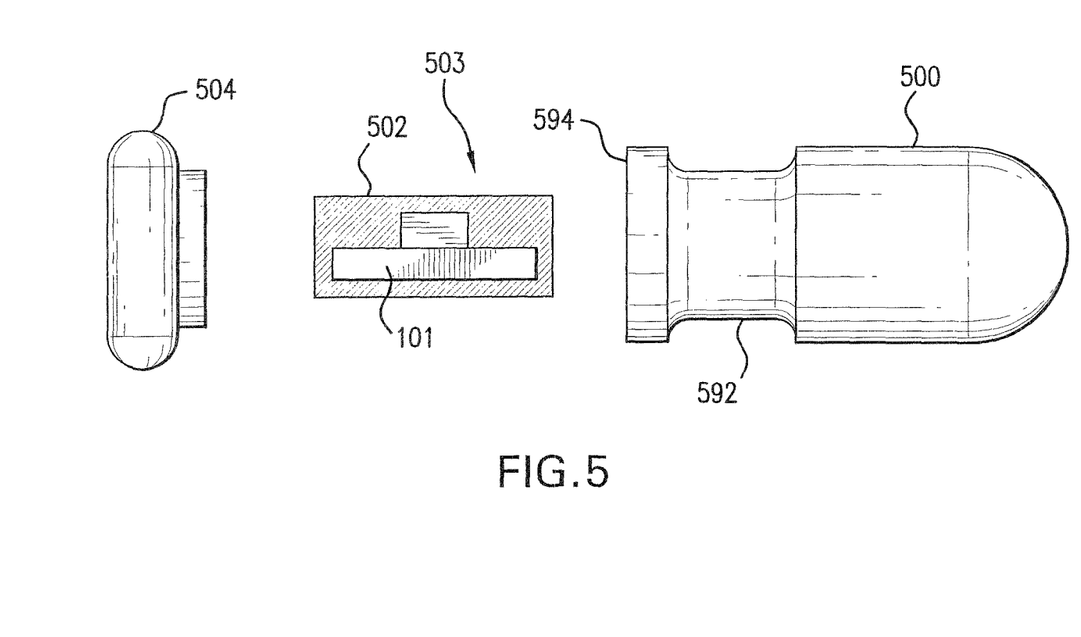
FIG. 5 is an exploded view of a circuit assembly according to an embodiment of the invention.

FIG. 4 is a flow chart illustrating a process 400, according to another embodiment, for creating circuit assembly 100. Process 400 may begin in step 402, where a housing 500 (e.g., a sleeve 500 or tube or other housing having an open end) (see FIG. 5) is created along with a plug 504 for plugging the opening in the housing. For example, a cylindrical sleeve 500 and plug 504 may be machined from a polymer rod, such as a rod of PMMA or other organic polymer. As shown in FIG. 5, sleeve 500 may have a notch 592 adjacent to the open end 594 of sleeve 500. If sleeve 500 and plug 504 are made from PMMA, the PMMA sleeve and plug may be annealed at approximately 80° C. for about four hours (step 403).

In step 404, epoxy is applied over the circuit 101 so that the circuit is partially or fully encased within an epoxy brick 502, thereby forming an assembly 503. In step 406, assembly 503, sleeve 500 and plug 504 are cleaned. For example, assembly 503, sleeve 500 and plug 504 may be cleaned by rubbing a Q-tip with IPA on the surfaces thereof. In step 408, an optical epoxy is prepared. EPO-TEK 301-2 Epoxy from Epoxy Technology of Billerica, Mass. and other epoxies may be used as the optical epoxy.

In step 410, the circuit encased within the epoxy brick (i.e., assembly 503) is placed into the sleeve 500. In step 412, the prepared optical epoxy is injected (i.e., introduced) into sleeve 500. Preferably, no bubbles in the optical epoxy are formed during step 412. In step 414, the plug 504 is placed into the open end of sleeve 500, thereby sealing the open end of the sleeve.

Figure 6:
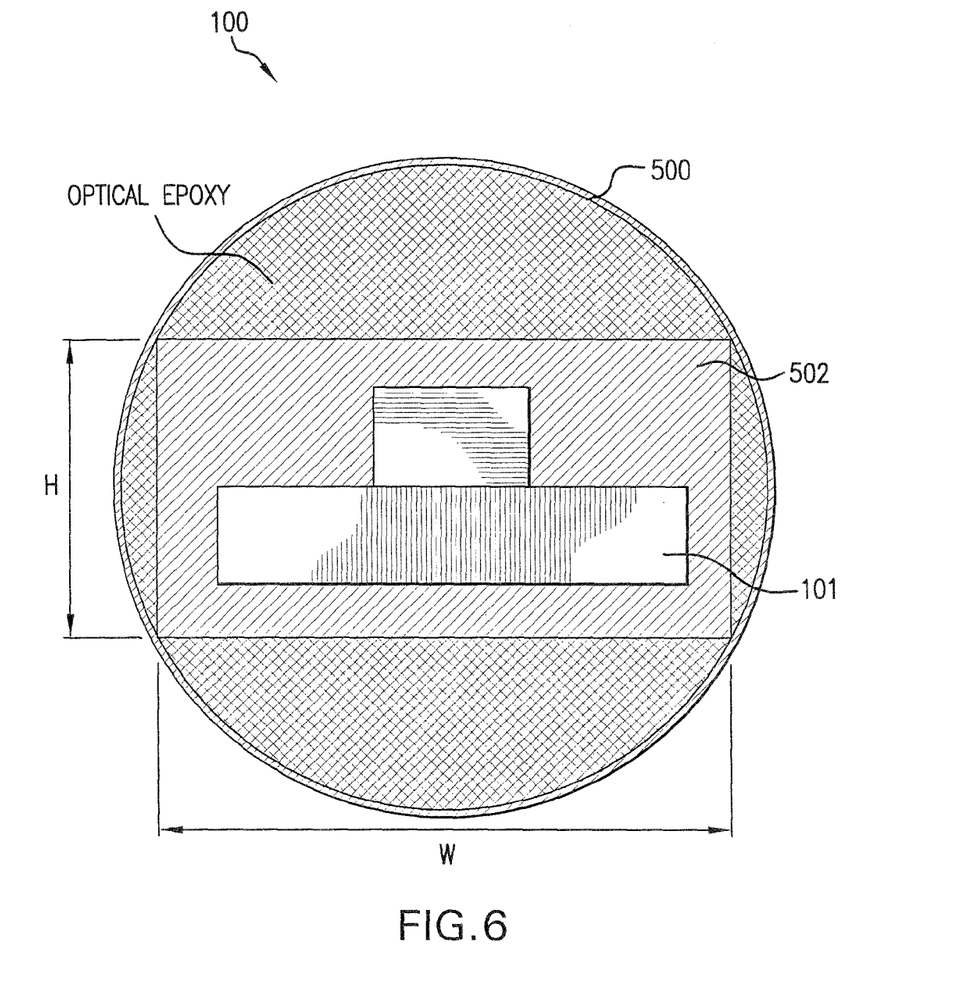
FIG. 6 is a cross sectional view of a circuit assembly according to another embodiment of the invention.

FIG. 6 is a cross sectional view, according to one embodiment, of the circuit assembly 100 along line A after step 414 is performed. In the embodiment shown in FIG. 6, the circuit 101 is fully encased within an epoxy brick 502. The epoxy brick 502, which houses circuit 101 is placed within sleeve 500, which may be a cylindrical sleeve. When sleeve 500 is a cylindrical sleeve and when circuit 101 is fully encased within the epoxy brick, it is preferable that the distance between the upper right hand corner and lower left corner of epoxy brick 502 be equal to or slightly less than the inner diameter of sleeve 502. That is, in some embodiments it is preferable that w=sqrt ((d*d)−(h*h)), where w is the width of assembly 503, h is the height of assembly 503, and d is the inner diameter of sleeve 500. In embodiments where the assembly 503 does not have a uniform width or has a circular shaped cross section, then the maximum width of the assembly may be equal to or slightly less than the inner diameter. As illustrated in FIG. 6, the optical epoxy (e.g., a refractive index (RI) matching epoxy) fills spaces between assembly 503 and sleeve 500.

Referring back to FIG. 4, in step 416, the new assembly (i.e., the sealed sleeve containing the epoxy and assembly 503) is placed into a pressure vessel. In step 418, the pressure within the vessel is increased to about 125 psi using Nitrogen or other inert gas. In step 420, the optical epoxy is cured for an amount of time (e.g., 20 hours) at a predetermined temperature (e.g., 40° C.). After the predetermined amount of time has elapsed, the assembly is removed from the pressure vessel and then final machined (step 422).

The method described above allows the possibility of annealing a PMMA housing before encasement without putting any additional stress on the circuit 101.

Figure 7:
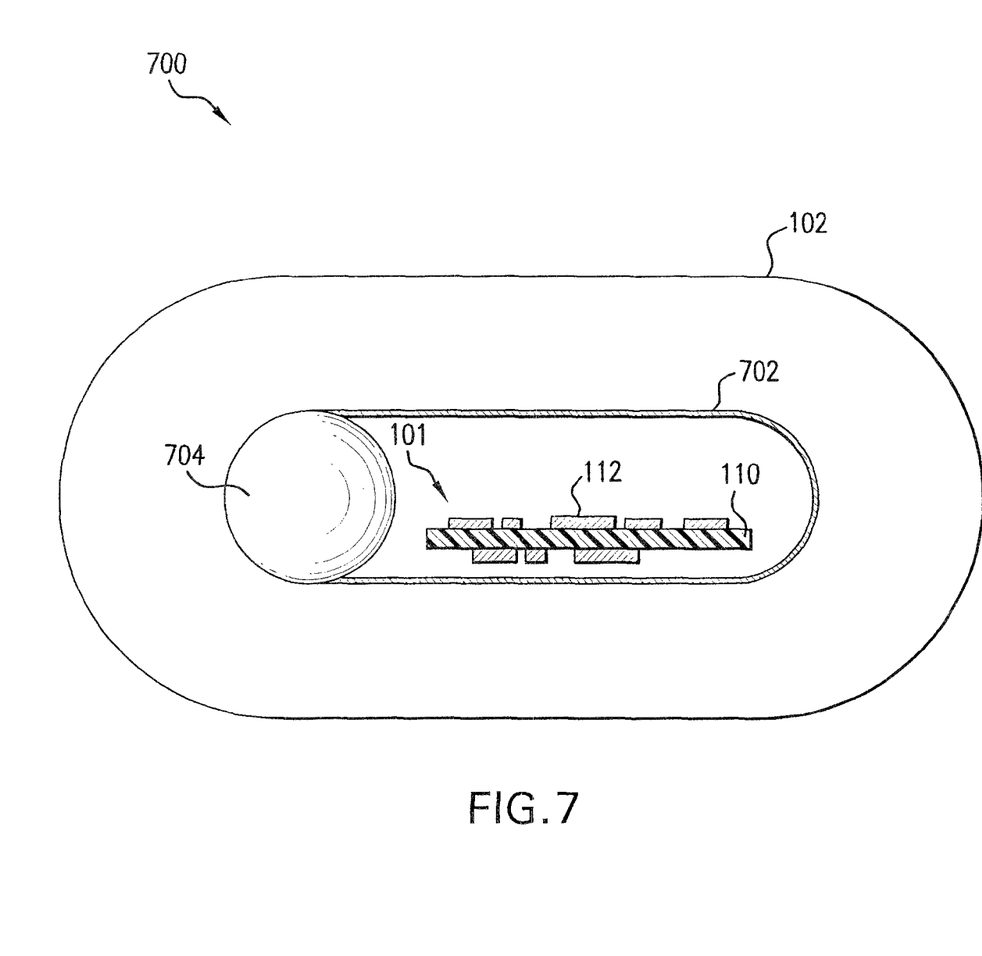
FIG. 7 illustrates a circuit assembly according to another embodiment of the present invention.
Figure 8:
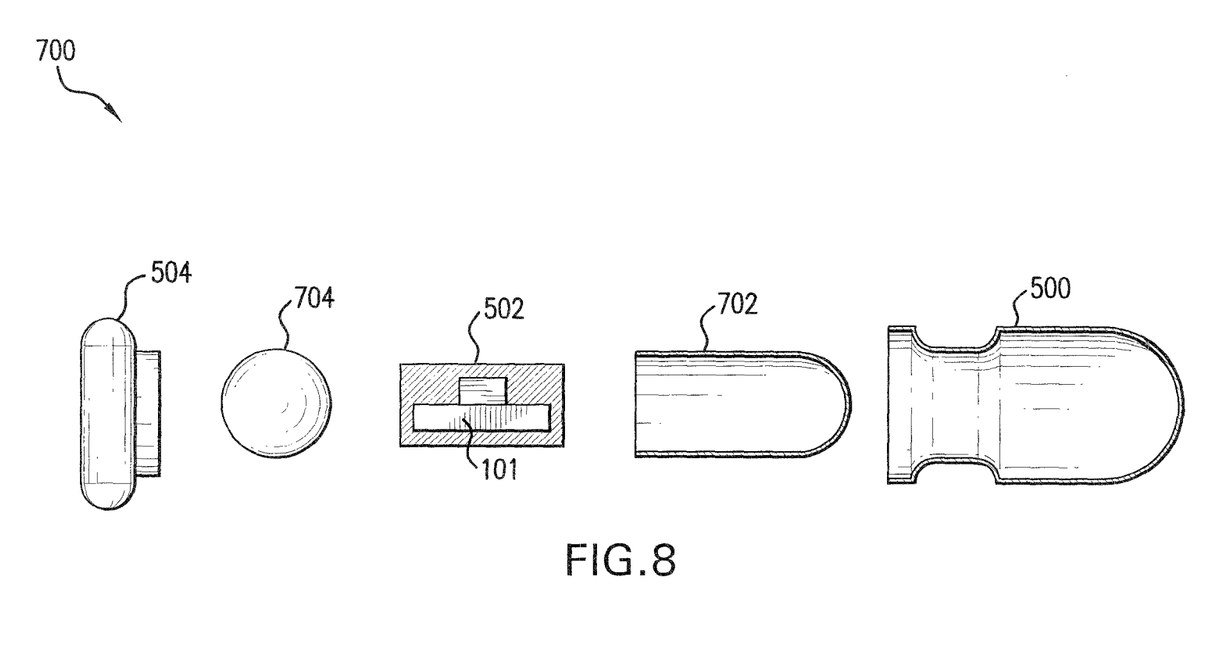
FIG. 8 is an exploded view of a circuit assembly according to another embodiment of the invention.

FIG. 7 illustrates an alternative circuit assembly 700 of the present invention. Circuit assembly 700 is similar to circuit assembly 100 in that assembly 700 includes a circuit 101 housed within a housing 102. However, in assembly 700, the circuit 101 is also housed within a glass housing 702 (e.g., a tube or other shaped housing), which itself is housed within the housing 102. The glass housing 702, in some embodiments, is closed at one end and open at the opposite end. The open end may be plugged by a glass ball 704 or other suitable plug. FIG. 8 is an exploded view showing the components of assembly 700, according to one embodiment. Glass housing 702, in some embodiments, may be constructed from an infra-red (IR) blocking glass.

Figure 9:
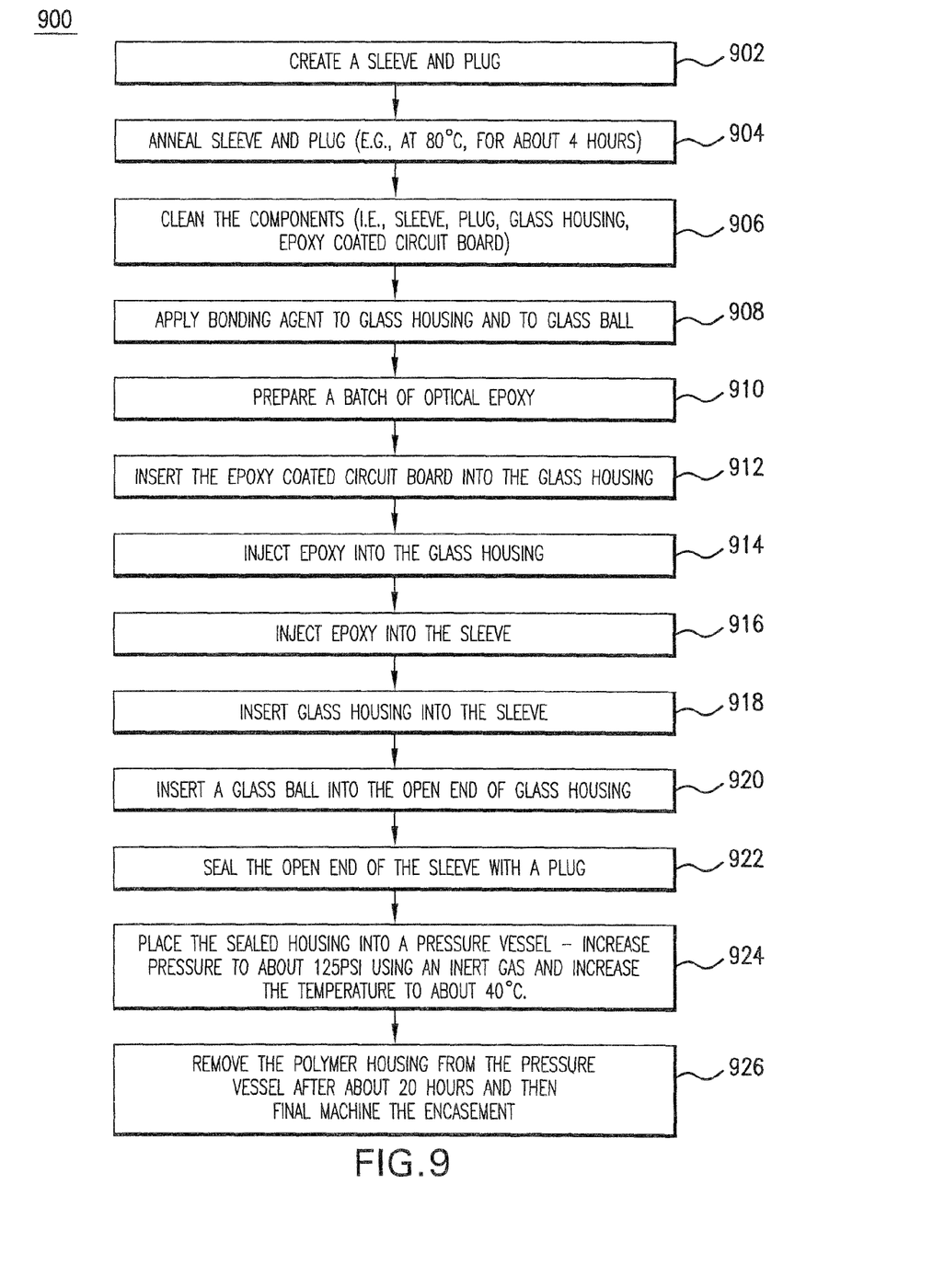
FIG. 9 is a flow chart illustrating a process, according to another embodiment, for encasing a circuit within a polymer housing.

FIG. 9 is a flow chart illustrating a process 900, according to one embodiment, for making assembly 700. Process 900 may begin in step 902, where a sleeve and a plug, such as sleeve 500 and plug 504, are created.

In step 904, the sleeve and plug are annealed. The sleeve and plug may be annealed at 80° C. for about four hours. In step 906, the components (e.g., sleeve 500, plug 504, glass housing 702, glass ball 704, epoxy brick 502, etc.) are cleaned. For example, sleeve 500 and plug 504 may be cleaned in an ultrasonic bath with IPA followed by a rinse step, and glass housing 702 and glass ball 704 may also be cleaned ultrasonically with KOH/alcohol solutions and then rinsed with water.

In step 908, a bonding agent is applied to the glass housing 702 and glass ball 704. The bonding agent used may be trimethoxy [2-(7-oxabicyclo [4.1.0]hept-3-yl)ethyl] silane, which may be purchased from Sigma-Aldrich Corporation (catalog no. 413321)

In step 910, a batch of optical epoxy is prepared. In step 912, the epoxy coated circuit board is inserted into the glass housing. In step 914, some of the prepared epoxy is injected into the glass housing 702.

In step 916, some of the prepared epoxy is injected into the sleeve 500. In step 918, glass housing 702, which houses the circuit, is inserted into an open end of the sleeve. In step 920, the glass ball 704 is inserted into the open end of glass housing 702, thereby sealing the open end of the glass housing. In step 922, the plug 504 is used to seal the open end of the sleeve.

In step 924, the sealed sleeve, which houses glass housing 702, which houses the circuit 101, is placed into a pressure vessel where the pressure is increased to about 125 psi using an inert gas and the temperature is increased to about 40° C. After about 20 hours, the pressure is gradually reduced and the assembly is removed from the pressure vessel and then final machined (step 926).

Although the above described processes are illustrated as a sequence of steps, it should be understood by one skilled in the art that at least some of the steps need not be performed in the order shown, and, furthermore, some steps may be omitted and additional steps added.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for fully encasing a circuit within a polymer housing, comprising:
    at least partially covering the circuit with an epoxy, wherein a sufficient amount of epoxy is used to cover the circuit so that the resulting surface topology is substantially smooth, some or all of the epoxy comprises a light blocking pigment, and the light blocking pigment is black;
    placing the epoxy-covered circuit in a mold;
    injecting a formulation comprising monomers and polymers into the mold; and
    polymerizing the formulation to form a fully-enclosed housing for the circuit;
    wherein the epoxy is located between the circuit and the polymerized formulation.

2. The method of claim 1, wherein the polymerization step is performed in a pressure vessel where the pressure is increased to at least about 125 psi using inert gas.

3. The method of claim 1, wherein the monomers are MMA monomers.

4. The method of claim 1, wherein the polymers are pre-polymerized PMMA.

5. The method of claim 1, wherein the monomers are MMA monomers, and the polymers are pre-polymerized PMMA.

6. The method of claim 1, wherein the formulation comprises between 60% and 80% pre-polymerized PMMA by volume.

7. The method of claim 1, wherein the formulation is injected into the mold so that the formulation surrounds the circuit.

8. The method of claim 4, wherein the formulation comprises between 60% and 80% pre-polymerized PMMA by volume.

9. The method of claim 6, wherein the formulation comprises 70% pre-polymerized PMMA by volume and 30% un-reacted MMA monomer into which the 70% pre-polymerized PMMA has been dissolved.

10. The method of claim 7, wherein the formulation completely surrounds the circuit.

11. A biocompatible, human implantable apparatus, comprising:
    a fully enclosed housing formed by a polymerized formulation of monomers and polymers;
    a circuit encased within the fully enclosed housing formed by the polymerized formulation of monomers and polymers, and
    an epoxy that at least partially covers the circuit in such a way that the epoxy-covered circuit has a surface topology that is substantially smooth, wherein some or all of the epoxy comprises a light blocking pigment, the light blocking pigment is black, and the epoxy is located between the circuit and the polymerized formulation.

12. The apparatus of claim 11, wherein the monomers are MMA monomers.

13. The apparatus of claim 11, wherein the polymers are pre-polymerized PMMA.

14. The apparatus of claim 11, wherein the monomers are MMA monomers, the polymers are pre-polymerized PMMA, and the formulation comprises between 60% and 80% pre-polymerized PMMA by volume.

15. The apparatus of claim 11, wherein the polymerized formulation surrounds the circuit.

16. The apparatus of claim 13, wherein the formulation comprises between 60% and 80% pre-polymerized PMMA by volume.

17. The apparatus of claim 14, wherein the formulation comprises 70% pre-polymerized PMMA by volume and 30% un-reacted MMA monomer into which the 70% pre-polymerized PMMA has been dissolved.

18. The apparatus of claim 15, wherein the polymerized formulation completely surrounds the circuit.

* * * * *